(12) United States Patent
Nishimura et al.

(10) Patent No.: US 8,058,409 B2
(45) Date of Patent: Nov. 15, 2011

(54) METHOD OF SERUM PRE-TREATMENT FOR GLYCOMIC ANALYSIS

(75) Inventors: Shin-Ichiro Nishimura, Sapporo (JP); Yasuro Shinohara, Sapporo (JP); Yoshiaki Miura, Sapporo (JP); Jun-ichi Furukawa, Sapporo (JP); Yoko Kita, Amagasaki (JP); Akio Takimoto, Amagasaki (JP); Mika Nakano, Amagasaki (JP)

(73) Assignees: National University Corporation Hokkaido University, Hokkaido (JP); Shionogi & Co., Ltd., Osaka (JP)

( * ) Notice: Subject to any disclaimer, the term of this patent is extended or adjusted under 35 U.S.C. 154(b) by 98 days.

(21) Appl. No.: 12/308,936

(22) PCT Filed: Jun. 29, 2007

(86) PCT No.: PCT/JP2007/063100
§ 371 (c)(1),
(2), (4) Date: Dec. 30, 2008

(87) PCT Pub. No.: WO2008/001888
PCT Pub. Date: Jan. 3, 2008

(65) Prior Publication Data
US 2009/0187011 A1    Jul. 23, 2009

(30) Foreign Application Priority Data
Jun. 30, 2006    (JP) .................... 2006-181292

(51) Int. Cl.
*C08H 1/00* (2006.01)
*C07C 233/00* (2006.01)
*C07C 309/62* (2006.01)
*C12Q 1/37* (2006.01)

(52) U.S. Cl. ............. 530/408; 530/409; 554/49; 435/23

(58) Field of Classification Search ................. None
See application file for complete search history.

(56) References Cited

U.S. PATENT DOCUMENTS
7,229,539 B1 * 6/2007 Lee et al. .................. 204/450
(Continued)

FOREIGN PATENT DOCUMENTS
WO    03/082811    10/2003
(Continued)

OTHER PUBLICATIONS

Helenius, A., et al., Solubilizatin of membranes by detergents, 1985, Current Contents, 1 page.*
(Continued)

*Primary Examiner* — Andrew D Kosar
*Assistant Examiner* — Yate K Cutliff
(74) *Attorney, Agent, or Firm* — Wenderoth, Lind & Ponack, L.L.P.

(57) ABSTRACT

A means for pre-treatment in glycomic analysis of a glycoprotein is provided by the present invention.
A salt of the general formula (I):

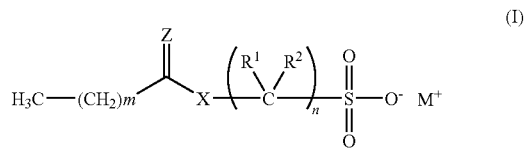

wherein $Z$, $X$, $R^1$, $R^2$, $M$, $m$ and $n$ are the same as described in DESCRIPTION,
is useful as a protein solubilizer, and an oligosaccharide is efficiently released from a sample if reductive alkylation and/or digestion by a proteinase are carried out under the presence of the said solubilizer at the first step in the glycomic analysis of glycoprotein derived from a living body.

5 Claims, 3 Drawing Sheets

U.S. PATENT DOCUMENTS

| | | | |
|---|---|---|---|
| 2005/0215456 A1* | 9/2005 | Goo et al. | 510/424 |
| 2006/0057659 A1* | 3/2006 | Bouvier et al. | 435/23 |
| 2006/0094000 A1* | 5/2006 | Mallet et al. | 435/4 |

FOREIGN PATENT DOCUMENTS

WO  03/102225  12/2003

OTHER PUBLICATIONS

Hikota, T., et al., Studies of Ester-containign surfactants: Effects of positoin of ester gorup o surface tension, 1974, Journal of the American Oil Chemists' Society, vol. 51, pp. 1-3 (3 pages).*

Imre, T., et al., Glycosylation site analysis of human alpha-1-acid glycoproteing (AGP) by capillary liquid chromatography-electrospray mass spectrometry, 2005, Journal of Mass Spectrometry, 40, pp. 1472-1483 (12 pages).*

Ross, A. R. S., et al., Identification of proteins from two-dimentional polyacylamide gels using novel acid-labile surfactant, 2002, Proteomics, 2, pp. 928-936 (9 pages).*

Edited byTthe Japanese Biochemical Society, Shinsei Kagaku Jikken Koza, vol. 1, Tanpakushitsu I, Bunri Seisei Seishitsu, Hakko, pp. 53-63, 1990.*

Tomofusa Tsuchiya, Method for the Extraction of Specialty Proteins, Sections 3.1 and 3.2, 1990, English translation of article Edited by The Japanese Biochemical Society pp. 53-63, attached translation includes cover & pp. 1-21.*

Form PCT/IB/338 together with International Preliminary Report on Patentability including translation of PCT Written Opinion dated Jan. 29, 2009 in International (PCT) Application No. PCT/JP2007/063100.

International Search Report dated Oct. 9, 2007 in the International (PCT) Application PCT/JP2007/063100 of which the present application is the U.S. National Stage.

Ram N. Mukherjea et al., "Hydroxy sulfonated fatty acid esters as surface active agents VI: Ester and amide derivative surfactants", Fette, Seifen, Anstrichmittel, 72(9), pp. 800-803, 1970.

* cited by examiner

METHOD OF SERUM PRE-TREATMENT FOR GLYCOMIC ANALYSIS

TECHNICAL FIELD

It is gradually clarified that an oligosaccharide of glycoconjugates widely distributed in the nature world is an important constituent of a living body and much involved in intercellular interaction. Accordingly many techniques of microquantitative glycomic analysis are developed in these days. The present invention is related to an agent to treat a sample isolated from a living body before structural analysis of the oligosaccharide and a method for pre-treatment thereof.

BACKGROUND ART

First of all release of a oligosaccharide from the protein is necessary in the glycomic analysis of the glycoconjugate and two methods are known; one of which is to enzymatically cleave an oligosaccharide using N-glycanase, for example, peptidyl N-glycosidase F(PNGase F), and the another one is to chemically hydrazinolyze the same.

Usually the enzymatic method is preferably employed rather than the chemical method since it is possible to cleave an oligosaccharide in the enzymatic method without depending a size or structure of the glycomic moiety in the substrate. However, there are various glycoproteins and a glycomic moiety is often surrounded by the secondary and/or the tertiary structure of a protein, and according to the result an enzymatic digestion by N-glycanase is frequently hindered.

In order to improve the efficacy of digestion by N-glycanase, various methods for pre-treating a sample are proposed using a reducing agent, a surfactant, a proteinase or the combination thereof.

A reductive alkylation can be an important method for pre-treatment to simplify the complicated tertiary structure of a protein and to promote the enzymatic digestion, and in such case solubilization of a protein is carried out by adding urea and a surfactant, for example, sodium dodecylsulfate (SDS) to the solution. But it is known that MS signal may be lowered if urea and/or SDS are not completely removed from the solution.

Other important method for the pre-treatment is a fragmentation of the protein moiety using a proteinase, for example, trypsin. This method is usually applied in a combination with the reductive alkylation described above, but trypsin digestion may be hindered if urea and/or SDS are not completely removed.

Recently an acidlysing surfactant (ALS) is newly developed as an alternative of urea or SDS (See, WO03/102225). It shows an enhancing effect on digestion by trypsin or PNGase F when added as a protein solubilizer, and mass analysis is never hindered since it can be decomposed under an acidic condition after digestive reaction is over. A sulfonate salt described below is already commercialized as a trademark of "RapiGest SF".

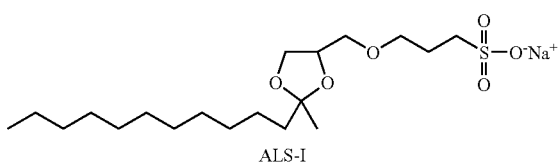

ALS-I

On the other hand, a sulfonate salt preferably used in the present invention is a kind of surfactants and use as a detergent is already known (See, WO03/082811). However, an enhancing effects on the reductive alkylation and the digestion by a proteinase described later and activity to release an oligosaccharide from glycoprotein are not known.

DISCLOSURE OF INVENTION

Problem to be Solved

A newly-developed protein solubilizer, "ALS", is characterized in that it is easily decomposed under an acidic condition and removed without difficulty. However, a labeled product such as 2-aminopyridyl derivative is widely used to increase detection sensitivity, and a ketone derivative generated after acid treatment of ALS may interfere with glycomic analysis in such case.

The objective of the present invention is to provide with a new protein solubilizer having the same solubilizing ability as ALS, which is stable under acidic condition and does not hinder glycomic analysis.

The other objective is to provide with a method for pre-treatment when analyzing an oligosaccharide of glycoprotein utilizing the said protein solubilizer.

Means for Solving Problem

The inventors have selected stable ALS analogs which are stable under acidic condition and extensively explored an analog which can release an oligosaccharide effectively from glycoprotein, after studying various combinations with a pre-treatment such as reductive alkylation or digestion by proteinase As the result, they found that compounds of the formula (I):

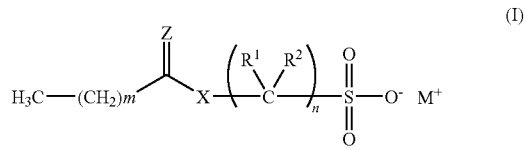

wherein Z is a oxygen atom or a sulfur atom; X is an oxygen atom or —N(R3)-; R3 is a hydrogen atom or a lower alkyl; R1 and R2 are independently a hydrogen atom or hydroxyl; M is a monovalent cation; m is an integer of 6-16 and n is an integer of 3-5,
filled the purpose above and further confirmed that they were useful as a protein solubilizer to complete the present invention.

Effect of Invention

The sulfonate salt of the present invention is useful as a protein solubilizer and can release an oligosaccharide moiety effectively from a sample especially when analyzing an oligosaccharide in glycoprotein of the living body by carrying out reductive alkylation and/or digestion by a proteinase using the said agent in the first step.

BEST MODE FOR CARRYING OUT THE INVENTION

Figure 1:
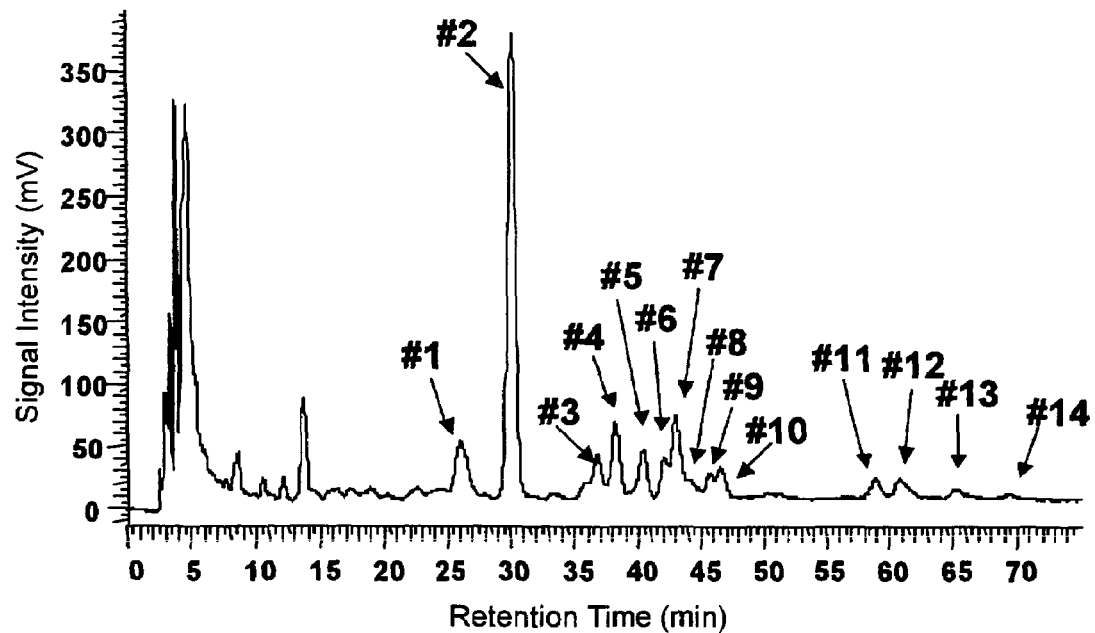
FIG. 1: It is a HPLC chromatogram when pre-treated under the condition of Example 3(2).

The solubilizer of the present invention includes sulfonate salts of the formula (I):

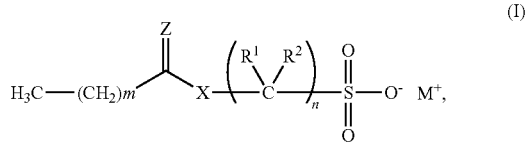

wherein Z is a oxygen atom or a sulfur atom; X is an oxygen atom or —N($R^3$)—; $R^3$ is a hydrogen atom or a lower alkyl; $R^1$ ad $R^2$ are independently a hydrogen atom or hydroxyl; M is a monovalent cation; m is an integer of 6-16 and n is an integer of 3-5. Among them it is preferable the compounds wherein Z is an oxygen atom, X is an oxygen atom or —NH— and —($CR^1CR^2$)n- is —$CH_2$—CH(OH)—$CH_2$—, and m is 8-14.

A term of "lower alkyl" includes a straight or branched chain of alkyl group having 1-6 carbon(s), and methyl, ethyl, propyl, isopropyl, n-butyl, sec-butyl, tert-butyl, n-pentyl, isopentyl and n-hexyl etc. are exemplified. "Monovalent cation" includes an alkali metal cation, and sodium, lithium and potassium etc. are exemplified.

An amide type agent such as PHL and PHM is preferable in the protein solubilizers provided by the present invention and a glycomic moiety of glycoprotein can be preferably analyzed by the agent in the combination with reductive alkylation and/or pre-treatment with proteinase described later, and further treated with N-glycanase, if necessary.

An ester-type compounds of the said sulfonate salts (I) can be prepared according to or based on the method described in WO 03/82811.

Also, a sulfonate salt (HSD) of the formula:

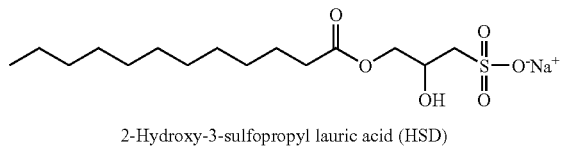

2-Hydroxy-3-sulfopropyl lauric acid (HSD)

can be commercially available.

Additionally an amide-type compound wherein Z is an oxygen atom and X is NH can be easily prepared according to the scheme described below:

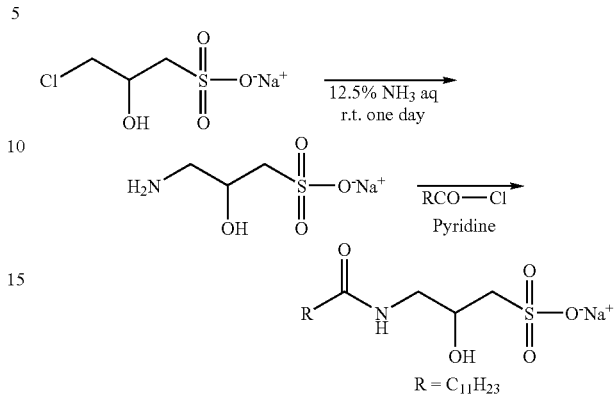

$R = C_{11}H_{23}$

In the case of a compound having lower alkyl amide ($R^3$ is a lower alkyl group), the product can be obtained by the reaction with lower alkyl amine in the place of $NH_3$ aqueous solution, and usually purified by recrystallization in the same manner as the ester-type compound.

It is not limited, but usually these sulfonate salt can be used as a protein solubilizer in the concentration of 0.001% to 10% in a sample solution. In the case of HSD, PHL and PHM, 0.4% to 0.004%, 0.4% to 0.004% and 0.4% to 0.0004% of the sulfonate salt can be usually added respectively.

The protein solubilizer of the present invention can be used as an additive when reductive alkylation of a glycoprotein sample is carried out. There is no limitation in the reductive alkylation and it can be carried out for example, by reacting with dithiothreitol (DTT) and iodoacetamide (IAA) as a reductive agent and alkylating agent respectively, for 30 minutes to 1-2 hours at room temperature to 60° C. Other examples of the alkylating agent include 2-mercaptoethanol, tri-n-butylphosphine and the like, and other examples of the alkylating agent include iodoacetic acid, iodomethane, ethyleneimine, 4-vinylpyridine and the like.

The protein solubilizer of the present invention can also be used when a sample is pre-treated with a proteinase. Especially in the case of analyzing an oligosaccharide in glycoprotein, any proteinase can be used if a glycomoiety in the sample is not changed, and fragmentation of the protein is possible using chymotrypsin, endopeptidase such as Asp-N, Glu-N or Lys-N as well as trypsin, which were used in the examples described below.

The protein solubilizer of the present invention also has an enhancing effect on releasing oligosaccharides from glycoprotein by N-glycanase such as PNGase F. The solubilizer of the present invention added in the first treatment step can be used repeatedly in the subsequent steps when it is used in the combination with reductive alkylation and/or pre-treatment with a proteinase, as shown in the following examples.

In addition, the protein solubilizer of the present invention can be widely used in hydrolysis of a protein as an additive and enhancing effect is expected if it is added in digestion of a protein sample using trypsin, chymotrypsin, or endopeptidase such as Asp-N, Glu-N or Lys-N etc.

Further, a solubilized protein can be easily prepared by adding the protein solubilizer of the present invention. As to the solubilized protein prepared above, reductive alkylation and any other reactions as well as hydrolysis described above can be preferably carried out Protocol of the pre-treatment of a sample according to the present invention is illustrated below but the present invention should not be construed to be limited thereto.

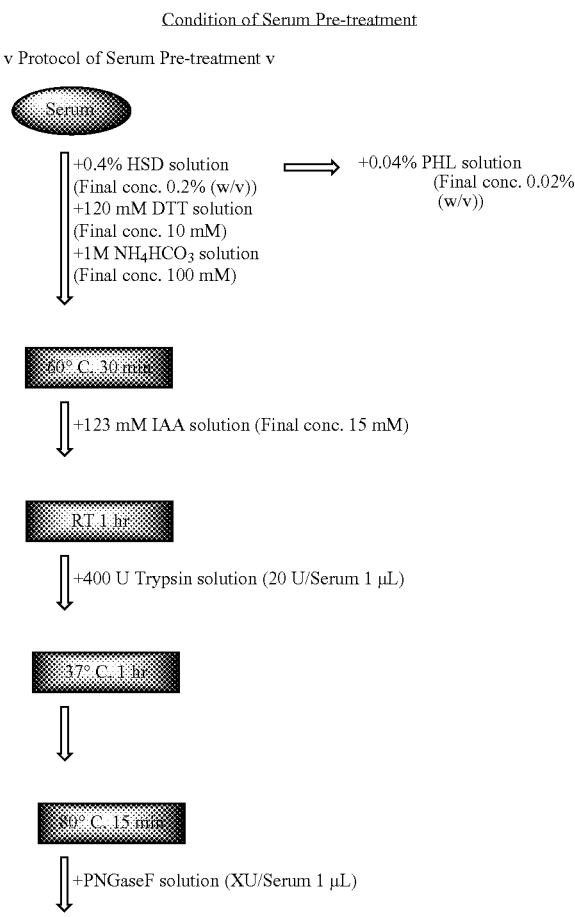

As shown in the scheme above, a solution of 0.4% HSD may be replaced with that of 0.04% PHL.

EXAMPLES

Example 1

Preparation of an Amide-Type Solubilization Agent PHL

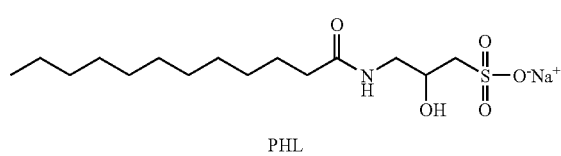

Sodium 3-chloro-2-hydroxypropanesulfonate (1.97 g, 10 mmol) was dissolved in 12.5% aq. ammonium solution and it was stirred at room temperature overnight. Ammonia was removed by concentrating the solution in evaporator and Sodium 3-amino-2-hydroxypropanesulfonate was obtained. Sodium 3-amino-2-hydroxypropanesulfonate (177 mg, 1 mmol) was dissolved in water (10 ml), NaHCO$_3$ (84 mg, 1 mmol) and lauroyl chloride (231 µl, 1 mmol) were added and the mixture was stirred at room temperature for 2 hours. After the reaction was completed, the compound was absorbed by adding Wakogel 50C18 (2 cm$^3$), the gel was loaded into a column and washed with water (50 ml), and eluted with methanol (10 ml). The elution was cooled to give PHL (sodium 2-hydroxy-3-lauramide-1-propansulfonate) as a crystalline. MALDI-TOF-MS [M+Na]$^+$ m/z=381.75.

Example 2

Preparation of an Amide-Type Solubilizing Agent PHM

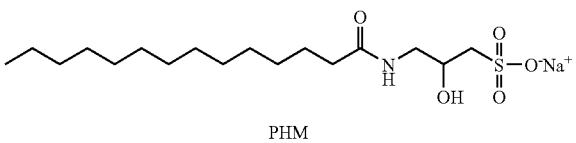

Myristoyl chloride was used in the place of lauroyl chloride to prepare PHM (sodium 2-hydroxy-3-myristamide-1-propanesulfonate) in the same manner as described above. MALDI-TOF-MS [M+Na]$^+$ m/z=409.84.

Example 3

Enhancing Effect of HSD on Releasing an Oligosaccharide

In order to confirm the effect of the solubilizer HSD of the present invention, it was combined with reductive alkylation (DTT and IAA) and digestion with a proteinase(trypsin) and efficiency of the release of N-glycans were compared.

Specifically a serum was treated by the method described below under Condition (1) to (7) and the released oligosaccharides were compared.

Condition (1):
A serum (20 µl) was diluted with a NH$_4$HCO$_3$ solution to give 50 µl of the total volume (Denaturation agent was not added).

Condition (2):
A serum (20 µl) was diluted with a NH$_4$HCO$_3$ solution and trypsin (400 U) was added. The mixture was incubated at 37° C. for an hour and then heated to 80° C. for 15 minutes to terminate the enzymatic reaction. The final volume was adjusted to 50 µl.

Condition (3):
A serum (20 µl) was diluted with a NH$_4$HCO$_3$ solution and DTT was added so that the final concentration was 10 mM. The mixture was left to stand at 60° C. for 30 minutes, then IAA was added so that the final concentration was 15 mM and the mixture was left to stand in a dark place at room temperature for an hour. Then trypsin (400 U) was added and the mixture was incubated at 37° C. for an hour and followed by heating to 80° C. for 15 minutes to terminate the enzymatic reaction.

The final volume was adjusted to 50 µl.

Condition (4):

A serum (50 µl) was diluted with an equal volume of Tris-HCl buffer solution containing 2% SDS and 2% 2-mercaptoethanol, and the mixture was left to stand at 95° C. for 5 minutes. Then an equal volume of 8% Triton X was added.

Condition (5):

A serum (20 µl) was diluted with a $NH_4HCO_3$ solution, ALS-1 and DTT were added so that the final concentrations were 0.1% and 10 mM respectively, and the mixture was left stand at 60° C. for 30 minutes. Then IAA was added so that the final concentration was 15 mM and the mixture was left to stand in a dark place at room temperature for an hour. The final volume was adjusted to 50 W.

Condition (6):

A serum (20 µl) was diluted with a $NH_4HCO_3$ solution, HSD and DTT were added so that the final concentrations were 0.2% and 10 mM respectively, and the mixture was left stand at 60° C. for 30 minutes. Then IAA was added so that the final concentration was 15 mM and the mixture was left to stand in a dark place at room temperature for an hour. The final volume was adjusted to 50 µl.

Condition (7):

A serum (20 µl) was diluted with a $NH_4HCO_3$ solution, HSD and DTT were added so that the final concentrations were 0.2% and 10 mM respectively, and the mixture was left stand at 60° C. for 30 minutes. Then LAA was added so that the final concentration was 15 mM and the mixture was left to stand in a dark place at room temperature for an hour. Then, trypsin (400 U) was added, the mixture was incubated at 37° C. for an hour and followed by heating to 80° C. for 15 minutes to terminate the enzymatic reaction. The final volume was adjusted to 50 µl.

A serum was treated under Condition (1) to (7) described above, PNGase F (2 U) was added [5 U only in the case of Condition (4)], the mixture was incubated at 37° C. for 24 hour and a reaction to release an oligosaccharide was carried out. The released oligosaccharide was digested with pronase, purified with a column, labeled fluorescently using 2-aminopyridine and analyzed with HPLC of an ODS column.

Chromatogram obtained under Condition (2) was shown at FIG. 1.

Figure 2:
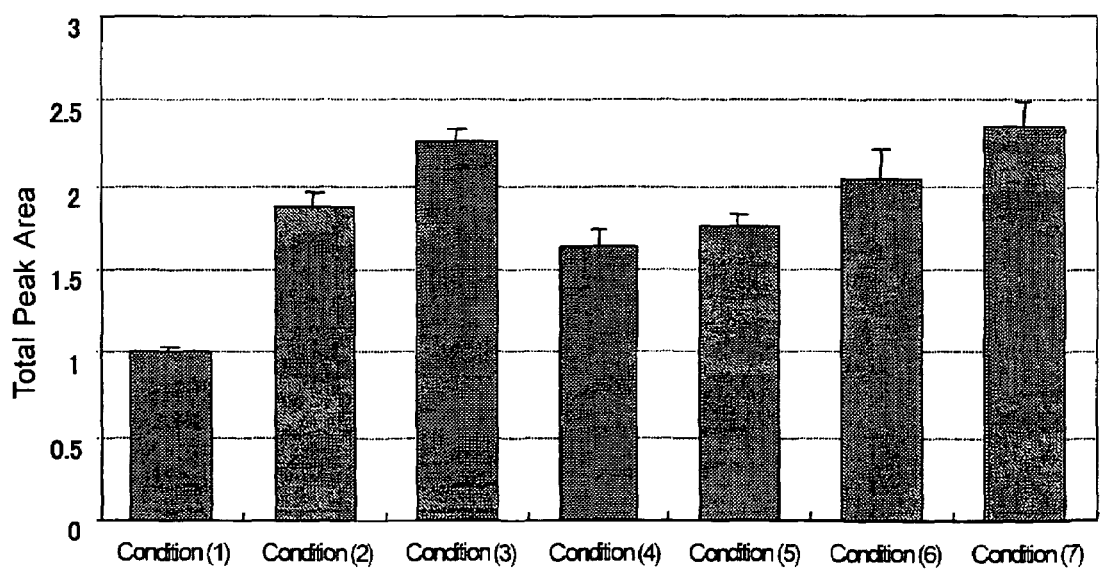
FIG. 2: It is a comparative graph showing total amounts of oligosaccharides released when pre-treated under the conditions of examples 3(1)-3(7).

A comparison of the total amount of released oligosaccharide (corresponding to the summation of area of peak #1 to peak #14) when treated under Condition (1) to (7) was illustrated in FIG. 2. They were shown in a relative amount when the amount of oligosaccharide in the case of Condition (1) was 1. The amounts of oligosaccharides released by PNGase F were remarkably different depending on the conditions of digestion. The efficiency to release an oligosaccharide was improved by about 88% under the trypsin-treatment [Condition (2)], and further improved by about 127% in the combination with reductive alkylation [Condition (3)]. The efficiency to release an oligosaccharide was also improved by about 63%, about 75% and about 104% respectively when the protein solubilizer of SDS [Condition (4)], ALS-1 [Condition (5)] and HSD [Condition (6)] were coupled with reductive alkylation, and the digestive efficiency was dependent on a sort of the solubilizer.

HSD, which was evaluated as a protein solubilizer for the first time, was shown to have the most efficient activity to release an oligosaccharide in the solubilizer studied. Further, the most efficient activity to release an oligosaccharide (improved by 134%) was observed when HSD-treatment was coupled with trypsin-treatment and reductive alkylation [Condition (7)].

Figure 3:
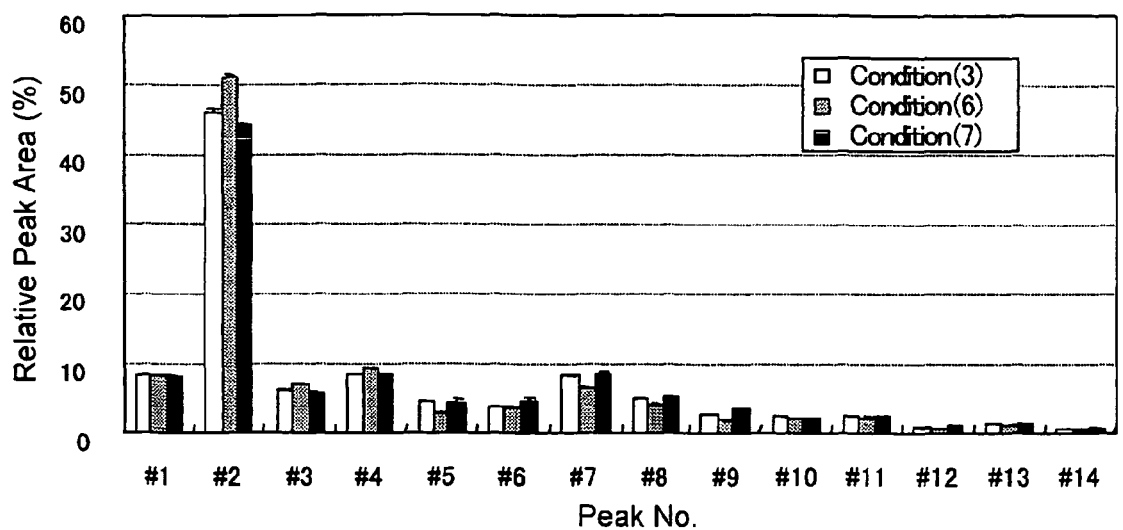
FIG. 3: It is a graph showing a relative ratio of amounts among oligosaccharides obtained when pre-treated under the conditions of (3), (6) and (7).
Figure 4:
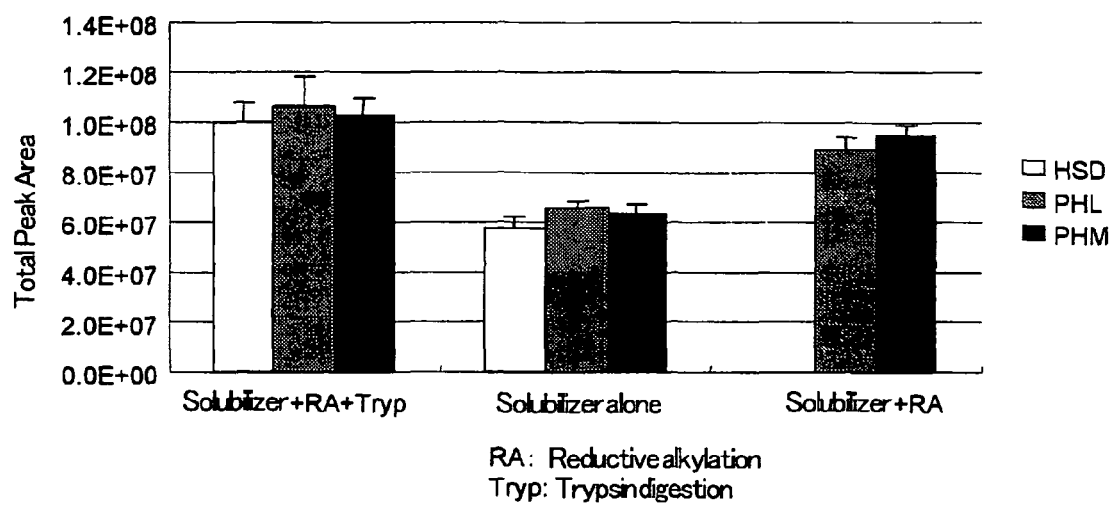
FIG. 4: It is a comparative graph showing total amounts of oligosaccharides released when a solubilizing agent HSD (2-hydroxy-3-sulfopropyl laurinate), PHL (sodium 2-hydroxy-3-laurylamide-1-propanesulfonate) or PHM (sodium 2-hydroxy-3-myristamide-1-propanesulfonate) is combined with treatments using reductive alkylation and a proteinase.
Figure 5:
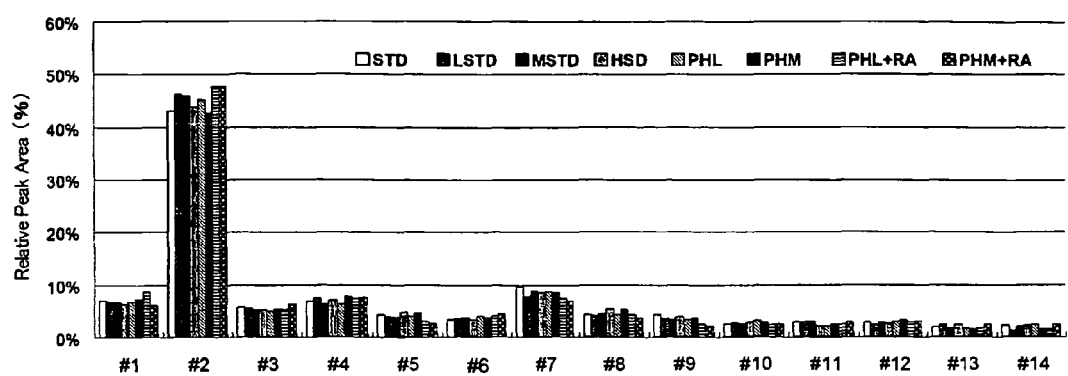
FIG. 5: It is a comparative graph showing effects of combinations of a solubilizing agent HSD, PHL or PHM with treatments using reductive alkylation and a proteinase in each peak of oligosaccharides. Refer to table 1 as to STD, LSTD, MSTD, HSD, PHL, PHL+RA and PHM+RA.

Quantitative profiles of the oligosaccharides released under three digestive conditions (3), (6) and (7) showing excellent efficacy to release an oligosaccharide were compared as to major fourteen peaks (See FIG. 3). As a whole, similar results were observed in the three conditions, but existence of a protein resistant to PNGase F was suggested if trypsin digestion was not carried out, since relative values of the peaks #5 to #14 were observed to decline without trypsin digestion.

Example 4

Comparison Among HSD, PHL and PHM

HSD, PHL and PHM were combined with reductive alkylation (DTT and LIA) and digestion with a proteinase (trypsin) and efficiencies of the release of N-oligosaccharides by PNGase F were studied. Specifically, a serum glycoprotein was digested with PNGase F after being treated under three different conditions described below.

Condition (1):

To a serum (20 µl), were added 4 µl of ammonium bicarbonate (100 mM, pH ca. 7.8) and 16 µl of the solubilizing agent (0.4% HSD, 0.04% PHL or 0.004% PHM) and left to stand at 60° C. for 30 minutes.

Condition (2):

To a serum (20 µl), were added 4 pd of 100 mM ammonium bicarbonate (pH ca. 7.8), 16 pd of the solubilizing agent (0.04% PHL or 0.004% PHM) and 8 µl of 50 mM DTT, and the mixture was heated at 80° C. for 15 minutes. 5 id of 135 mM iodoacetamide (IAA) aq. solution was added and left to stand in a dark place at room temperature for an hour.

Condition (3):

To a serum (20 µl), were added 4 µl of 100 mM ammonium bicarbonate (pH ca. 7.8), 16 µl of the solubilizing agent (0.4% HSD, 0.04% PHL or 0.004% PHM) and 8 µl of 50 mM DTT, and the mixture was heated at 80° C. for 15 minutes. 5 µl of 135 mM iodoacetamide (IAA) aq. solution was added and left to stand in a dark place at room temperature for an hour. Further, 5 µl of trypsin (400 U) was added and the mixture was incubated at 37° C. for an hour. Then the mixture was heated at 80° C. for 15 minutes to inactivate trypsin.

PNGase F (2 U) was added to each serum treated under Condition (1) to (3) described above and the mixture was incubated at 37° C. for 24 hour. Then it was heated at 90° C. for 15 minutes to inactivate PNGase F and the volume of each sample was adjusted to 200 µl by adding 100 mM ammonium bicarbonate.

After PNGase F-digestion, 50 µl of each sample was digested with 50 µg of pronase and the fraction of oligosaccharide was purified by Biogel P4 column. The oligosaccharide was pyridylaminated according to the conventional method and isolated from excess reagent using Sephadex G-15 column. After evaporation of the reagent under reduced pressure, the residue was dissolved in 500 µl of $H_2O$, and 5 µl of the aqueous solution was injected to HPLC. Quantitative determination of the oligosaccharide was performed with an established reversed phase HPLC, and efficiency of releasing an oligosaccharide and quantitative oligosaccharide profile under each digestive condition were compared based on the peak areas of major fourteen peaks.

Result was shown in the next table.

| STD (JST) | LSTD | MSTD | HSD | PHL | PHM | PHL + RA | PHM + RA |
|---|---|---|---|---|---|---|---|
| Serum<br>+0.4% HSD<br>+DTT<br>↓ | Serum<br>+0.04% PHL<br>+DTT<br>↓ | Serum<br>+0.004% PHM<br>+DTT<br>↓ | Serum<br>+0.4% HSD<br>↓ | Serum<br>+0.04% PHL<br>↓ | Serum<br>+0.004% PHM<br>↓ | Serum<br>+0.04% PHL<br>+DTT<br>↓ | Serum<br>+0.004% PHM<br>+DTT<br>↓ |
| 60° C. 30 min | 60° C. 30 min | 60° C. 30 min | 60° C. 30 min | 60° C. 30 min | 60° C. 30 min | 80° C. 15 min | 95° C. 5 min |
| +IAA<br>↓ | +IAA<br>↓ | +IAA<br>↓ | | | | +IAA<br>↓ | +IAA<br>↓ |
| RT 1 hr | RT 1 hr | RT 1 hr | | | | RT 1 hr | RT 1 hr |
| +Tryp<br>↓ | +Tryp<br>↓ | +Tryp<br>↓ | | | | | |
| 37° C. 1 hr | 37° C. 1 hr | 37° C. 1 hr | | | | | |
| ↓ | ↓ | ↓ | | | | | |
| 80° C. 15 min | 80° C. 15 min | 80° C. 15 min | | | | | |

DTT: Dithiothreitol
IAA: Iodoacetamide
Tryp: Trypsin
(n = 3)

There was no significant difference in the digestive efficiency or quantitative profile under any of digestive condition (1), (2) and (3), even if a sort or concentration of the solubilizer was changed.

INDUSTRIAL APPLICABILITY

The protein solubilizer in the present invention has a function as a protein denaturant and enhance a digestive reaction by various enzymes. It also enhances N-glycanase and a reaction in other pre-treatment, and the agent is remarkably useful as an additive of pre-treatment for glycomic analysis.

The invention claimed is:

1. A method for release of oligosaccharide from a glycoprotein comprising a step to treat a sample with N-glycanase under the presence of a protein solubilizer comprising a salt of the formula:

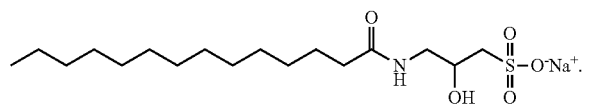

2. A method for release of oligosaccharide from a glycoprotein comprising
   1) a step to treat a sample with reductive alkylation under the presence of a protein solubilizer comprising a salt of the formula:

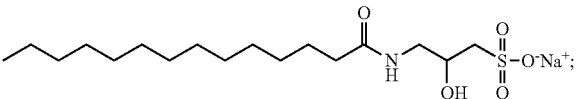

2) a step to treat the sample with proteinase and
   3) a step to treat the sample with N-glycanase.

3. The method according to claim 1, wherein the N-glycanase is peptide N-glycosidase F.

4. The method according to claim 2, wherein the proteinase is trypsin, chymotrypsin, lysyl endopeptidase, endoproteinase Glu-C or endoproteinase Asp-N.

5. The method according to claim 2, wherein the N-glycanase is peptide N-glycosidase F.

* * * * *